United States Patent
Nisch et al.

(10) Patent No.: US 6,298,270 B1
(45) Date of Patent: Oct. 2, 2001

(54) RETINA IMPLANT

(75) Inventors: Wilfried Nisch, Tübingen; Martin Stelzle, Reutlingen; Stefan Weiss; Eberhart Zrenner, both of Tübingen; Alfred Stett, Reutlingen; Heinz Gerhard Graf, Magstadt; Michael Graf, Waiblingen; Markus B. Schubert, Tübingen; Harald N. Wanka, Remshalden/Geradstetten; Anke Hierzenberger, Sindelfingen, all of (DE)

(73) Assignee: Eberhard-Karls-Universitat Tubingen Universitatsklinkum (DE)

( * ) Notice: Subject to any disclaimer, the term of this patent is extended or adjusted under 35 U.S.C. 154(b) by 0 days.

(21) Appl. No.: 09/298,684

(22) Filed: Apr. 23, 1999

Related U.S. Application Data

(63) Continuation-in-part of application No. PCT/EP97/05700, filed on Oct. 16, 1997.

(30) Foreign Application Priority Data

Oct. 23, 1996 (DE) .............................................. 196 44 114
Feb. 17, 1997 (DE) .............................................. 197 05 988

(51) Int. Cl.$^7$ .................................................. A61N 1/18
(52) U.S. Cl. .............................................................. 607/54
(58) Field of Search ............................. 607/54, 116, 148; 623/6.63; 128/898

(56) References Cited

U.S. PATENT DOCUMENTS

| 4,628,933 | 12/1986 | Michelson . | |
|---|---|---|---|
| 5,024,223 | * 6/1991 | Chow | 607/53 |
| 5,895,415 | * 4/1999 | Chow et al. | 607/54 |
| 6,032,062 | * 2/2000 | Nisch | 600/372 |

FOREIGN PATENT DOCUMENTS

| P44247532 | 1/1996 | (DE) . |
| 195 29 371.1 | 2/1997 | (DE) . |
| 0 460 320 A2 | 11/1991 | (EP) . |
| 90308575.1 | 11/1991 | (EP) . |
| PCT/EP 97/05700 | 10/1997 | (WO) . |

OTHER PUBLICATIONS

John Wyatt, Joseph Rizzo, *Ocular Implants For the Blind*, May 1996, from IEEE Spectrum, pp. 47, 50–53, 68–69.

* cited by examiner

Primary Examiner—George Manuel
(74) Attorney, Agent, or Firm—Oppenheimer Wolff & Donnelly LLP; Claude A. S. Hamrick

(57) ABSTRACT

A retina implant has a substrate with a surface for applying same to a retina. The substrate comprises electrodes for stimulating cells within the retina. The electrodes are provided on the surface and are exposed to visible light impinging on the retina such that stimuli are exerted on the cells by the electrodes. The implant, further, comprises a photovoltaic layer responsive to non-visible light. The stimuli are locally switched utilizing a voltage generated by the photovoltaic layer.

22 Claims, 2 Drawing Sheets

RETINA IMPLANT

This application is a Continuation-in-Part of International Application No. PCT/EP97/05700, filed Oct. 16, 1997, German Patent No. 197 05 988.0, filed Feb. 17, 1997 and German Patent No. 196 44 114.5, filed Oct. 23, 1996.

FIELD OF THE INVENTION

The present invention relates to the field of retina implants, in particular to epiretinal and subretinal implants having a substrate with a surface for applying the implant with that surface to the retina, and wherein the substrate comprises electrodes for stimulating cells within the retina. The electrodes are provided on the surface and are exposed to visible light entering into the eye and impinging on the retina such that stimuli are exerted on the cell by way of the electrodes.

BACKGROUND OF THE INVENTION

Retina implants of various kinds are well-known in the prior art. For example, European published patent application 0 460 320 discloses a subretinal implant to be implanted between lower layers of the retina. This prior art implant essentially consists of a silicon chip configured by a large number of densely packed microphotodiodes. The photoactive surface of the photodiodes is directed to the light impinging through the eyes on the retina. The photodiodes generate an amplitude modulated current stimulating the cellular layer of the retina lying on the implant surface. By using such implant it shall be possible to enable patients suffering from retinal degenerations to improve or even regain vision.

The prior art implant is configured such that the impinging ambient light shall be sufficient to generate the required stimuli for the retinal cells. Hence, an external energy supply is not provided.

In the scientific journal IEEE Spectrum of May 1996, pp. 47–53, still another retina implant is disclosed which, however, shall be used as an epiretinal implant. Consequently, this prior art implant has an electrode surface which is placed between the vitreous body of the eye and the retina surface for stimulating ganglion cells located just below the retina surface.

In contrast to the situation with subretinal implants, when epiretinal implants are used, it is necessary to encode the stimuli in order to compensate for the biological variations to which the biological signals are subjected on their way between the photoreceptors and the ganglion cells in the lower retinal layers. Epiretinal implants are, therefore, controlled externally, namely on the basis of an image which, for example, is generated by a video camera or the like which, in turn, may be configured as spectacles for a patient.

in view of these systematic distinctions between subretinal implants and epiretinal implants, the latter are larger in view of their specific design, are more complicated and have a higher energy consumption.

In the prior art epiretinal implant mentioned before, the image viewed by the patient is recorded by means of a CCD-camera which, together with a signal processing chip and a laser are provided in a spectacle-like device.

Within the implant itself the electrode array that is provided for stimulating the ganglions, is configured as a thin blade extending laterally from the implant as such. The blade is placed on the retina. The implant body as such is configured relatively bulky. Further to a stimulator chip it comprises a photodiode array being directed against the eye opening. The photodiode array receives a light signal from the laser being arranged in the spectacle-like device. The light signal is within the visible portion of the spectrum and contains the image signals on the one hand side and, further, light energy used for the implant energy supply.

It is, therefore, a disadvantage of this prior art epiretinal implant that a considerable portion of the surface in the area of the retina must be obscured by the photodiode array in order to ensure the necessary signal transmission and power supply. That portion of the retina which is obscured by the implant may, hence, not used for stimulation. Further, the amount of energy that may be transmitted into the eye is limited by the physiological threshold of the retina with respect to visible light.

In a subretinal implant of the kind mentioned at the outset, the problem is that ambient light may be insufficient to generate stimuli of sufficient amplitude being larger than the stimulus threshold of the retinal cells to be stimulated.

It is, therefore, an object underlying the invention to improve an implant of the kind mentioned at the outset such that even under poor ambient light conditions there is sufficient energy available to generate stimuli of required amplitude. When doing so the disadvantages shall be avoided associated to epiretinal implants of the kind discussed above and consisting mainly in that certain areas of the retina may not be used for stimulation because they are obscured by implant components.

SUMMARY OF THE INVENTION

These and other objects of the invention are solved by an implant of the kind mentioned above having a substrate with a first surface for applying same to a retina, wherein the substrate comprises electrodes for stimulating cells within the retina, the electrodes being provided on the surface and being exposed to visible light impinging on the retina such that stimuli are exerted on the cell by the electrodes, wherein, further, a first layer, being a photovoltaic layer responsive to non-visible light is provided and the stimuli are locally switched utilizing a voltage generated by the layer.

The object underlying the invention is thus entirely solved.

The invention makes use of the fact that for solving the object it is recommendable to effect the energy supply that is required for stimulation by infrared light. The optical elements as well as the retina of the human eye is permeable to infrared light. Therefore, even with sufficient high intensities no damage to the retina must be expected. The supply power being available within the eye may additionally be enhanced by effecting the infrared coupling on a global basis, i.e. over the maximum possible surface area of the retina or the implant, respectively, whereas the cells on the other hand side are exclusively stimulated locally.

In order to be independent from the available ambient light as well as from the physiological threshold of the retina with respect to visible light, non-visible light, preferably infrared light, is used for providing the required energy for generating the stimuli.

The power supply for the implant according to the present invention is, hence, independent from the available ambient light and is, further, independent of the fact whether the viewed image has a high or a low brightness.

In a preferred embodiment of the invention the electrodes, in a top plan view on the substrate, are surrounded by the photovoltaic layer.

This measure has the advantage that by setting the surface ratio between electrodes and photovoltaic layer accordingly, the surface area of the photovoltaic layer may be set in a predetermined manner. Preferably, the electrodes occupy a surface portion of between 10% and 50%.

In another preferred embodiment of the invention the electrodes comprise a switch adapted to be actuated optically and feeding through the voltage as the stimulus when being in a closed state.

This measure has the advantage that the implant generates the stimuli on exactly those points on the implant surface corresponding to the effectively viewed image.

In a first modification of this embodiment the switch is configured as an area in a second layer of the substrate, the second layer being electrically non-conductive when exposed to the non-visible light and being electrically conductive when exposed to the visible light.

This measure has the advantage that the electrode surface is exactly just as large as it corresponds to the bright, i.e. to the to-be-stimulated areas of the entire image. In all dark areas of the image in which no stimulation of the cells shall be effective, the non-visible light may be used for generating additional energy.

In this context it is further preferred in another embodiment of the invention to use amorphous, hydrogenized silicon (a-Si:H) as a material for the second layer. However, one may also use alloys of amorphous, hydrogenized silicon, for example alloys with carbon (a-SiC:H) or germanium (a-SiGE:H).

In still another group of embodiments of the invention the electrodes comprise contact surfaces being configured as a layer of a material being impermeable for the non-visible light.

This measure has the advantage that at a specific point of the electrode a stimulation may be effected when visisble light impinges, however, may not be effected by non-visible light having the sole purpose of supplying energy.

Implants according to the present invention may alternately be used as subretinal implants or as epiretinal implants. In the latter case it is only necessary to configure the implant as being permeable for visible light.

In other groups of embodiments of the present invention the implant comprises a substrate having through openings.

This measure has the advantage that in particular in a subretinal implant the supply of the retina with nutrients is improved because the supply may be effected through the through openings.

The through openings may, alternately, be provided in a rigid substrate, however, one may also configure the substrate to be flexible or be a net from a flexible carrier material.

In the latter case one does not only have the advantage of a better nutrient supply for the retina. Further to that one has the advantage that due to the use of flexible material the implant may better be adapted to the shape of a retina.

Further advantages will become apparent from the description and the enclosed drawing.

It goes without saying that the features discussed before and those that will be explained hereafter may not only be used in the particularly given combination but also in other combinations or alone without leaving the scope of the present invention.

BRIEF DESCRIPTION OF THE DRAWINGS

Exemplary embodiments of the invention are shown in the drawing and will be described in further details in the subsequent description of preferred embodiments.

DETAILED DESCRIPTION OF THE PREFERRED EMBODIMENTS

Figure 1:
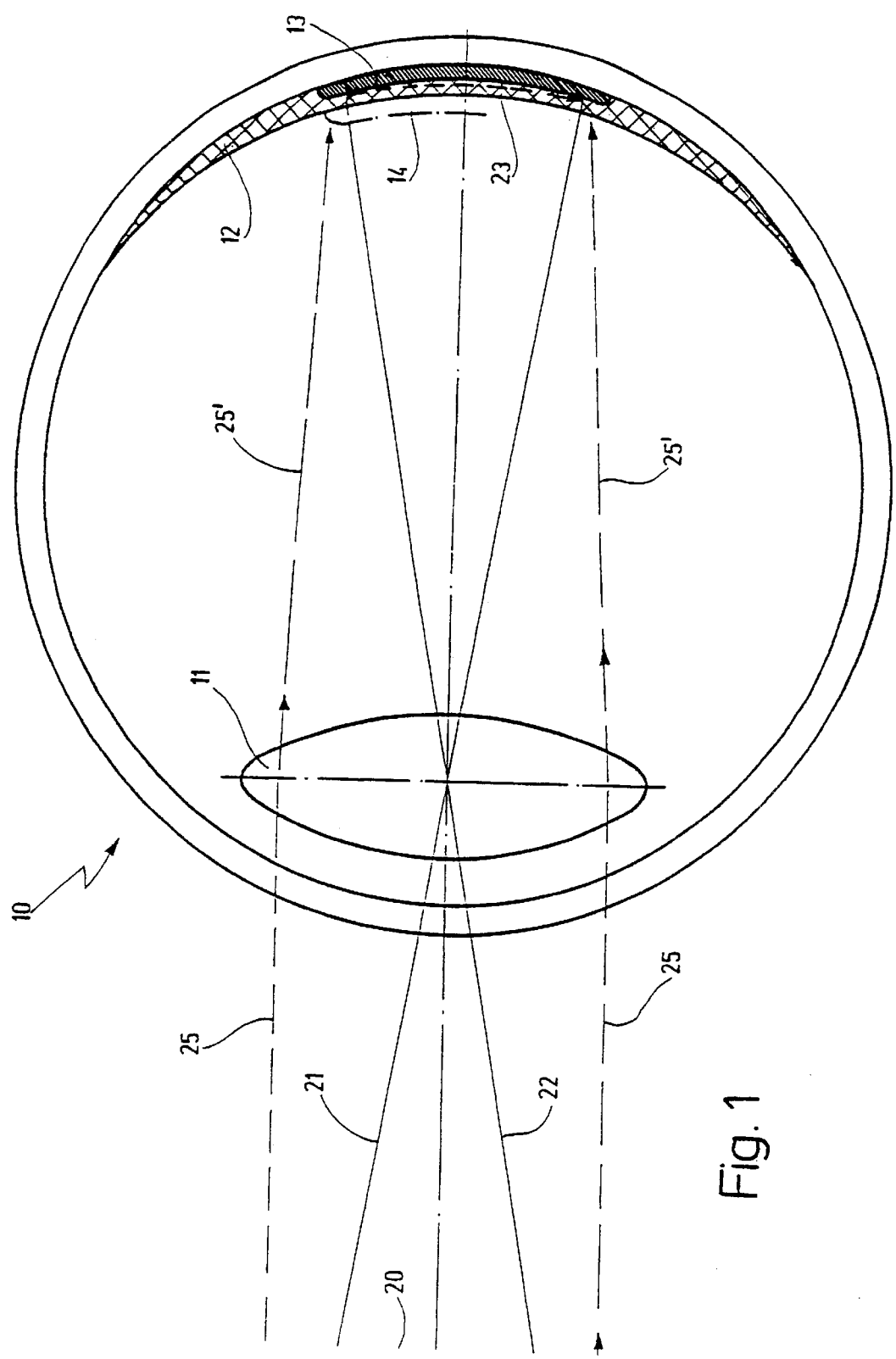
FIG. 1 shows an extremely schematic cross-sectional view through an eye, the retina of which being provided with an implant according to the present invention.

In FIG. 1 10 as a whole designates an eye, for example a human eye. Within eye 10 a lens 11 as well as a retina 12 are schematically shown.

A subretinal implant is shown at 13, implant 13 being located within lower layers of retina 12. An epiretinal implant is indicated at 14 with dash-dot line. Epiretianl implant 14 is placed on the retinal surface.

An object 20 is imaged through lens 11 on retina 12 in the usual fashion, as indicated with rays 21, 22 and an upside-down image 23.

In FIG. 1 25 indicates a ray beam of non-visible light, in particular infrared light. Light beam 25 is configured such that it impinges on the entire surface of implant 13 or 14, respectively. For that purpose light beam 25 is only slightly modified by lens 11, as indicated by 25' in eye 10. A focusing of light beam 25 shall be avoided in order to prevent local warming up within the interior of eye 10. Light beam 25 is only indicated schematically. Due to the wavelength of infrared light ($\lambda < 1$ $\mu$m) the source of infrared light must be located directly in front of the outer focus of lens 11.

Figure 2:
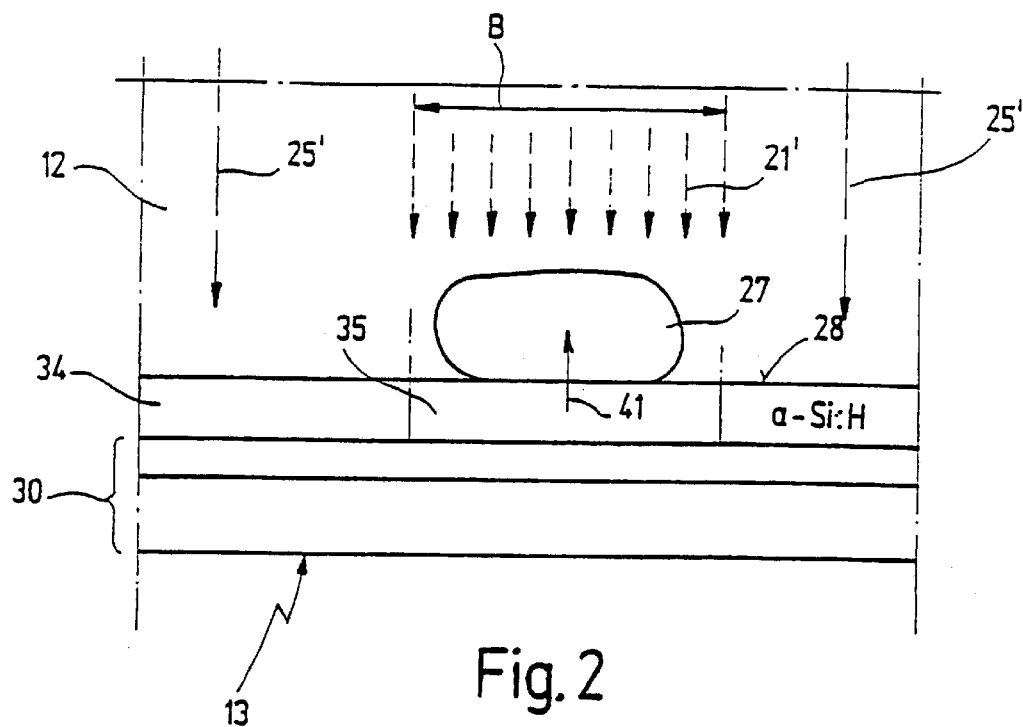
FIG. 2 shows a lateral cross-section of a portion of the retina in a subretinal arrangement on a highly enlarged scale.

In FIG. 2 implant 13 may be seen essentially below the surface of retina 12, i.e. in a subretinal position. 27 indicates a single cell of retina 12. Cell 27 is contacted at its lower surface by a surface 28 of implant 13.

The layer structure of implant 13 is as follows:

The lowermost layers are configured by an infrared diode 30. Infrared diode 30 may, alternately, consist of crystalline silicon and, for example, be configured by a P-N- or a N-P-transition. However, also free-layered configurations N-I-P or P-I-N (seen in an upward direction) are possible. Surface 28 of implant 23 is configured by an amorphous layer 34 made of hydrogenized silicon (a-Si:H). Such layers are well-known in the art. For example they contain between 2% and 10% hydrogen within the silicon. Infrared diode 30, however, may also consist of an hydrogenized silicon alloy, for example a-SiGe:H or of microcrystalline silicon in a structure.

In this context it is important that a relatively highly doped layer is provided below that plane through which the stimulus shall be exerted, in the shown example below amorphous layer 34. The highly doped layer shall have a sufficiently high lateral conductivity in order to be able to conduct current to the point of stimulation . 25' in FIG. 2 again indicates an infrared light beam impinging on the entire surface 28. Amorphous layer 34 is permeable for infrared light 25', however, it is only weakly doped or not doped at all. As long as infrared light 25' impinges on amorphous layer 34, the conductivity of amorphous layer 34 is very low, i.e. it acts as an isolator.

B in FIG. 2 indicates that with a particularly viewed image a certain area B is subjected to visible light 21'.

When visible light 21' impinges on amorphous layer 34, the conductivity of the latter abruptly increases by several orders of magnitude.

As a consequence an area of extremely good electrical conductivity is generated within a local area 35 of amorphous layer 34, corresponding just the width B in the schematic representation of FIG. 2. Area 35, therefore, acts like an optically controlled electrical switch.

Due to the impinging infrared light 25' infrared diode 30 is in a situation of supply current being essentially higher as compared to the purely visible excitation. If, as described above, area 35 "feeds through", a stimulation occurs on cell 27 lying on area 35, as indicated by an error 41. As already mentioned, below this location (arrow 41) there should be a relatively highly doped layer enabling a sufficiently high lateral conductivity, i.e. a lateral conduction of current to the point of stimulation.

The potential of stimulus 41 does not only correspond to the optical energy impinging on area B. Instead, the entire surface being illuminated by visible light at a particular moment, maybe used. As a consequence even under very weak illumination conditions it is possible to locally generate high stimuli.

Figure 3:
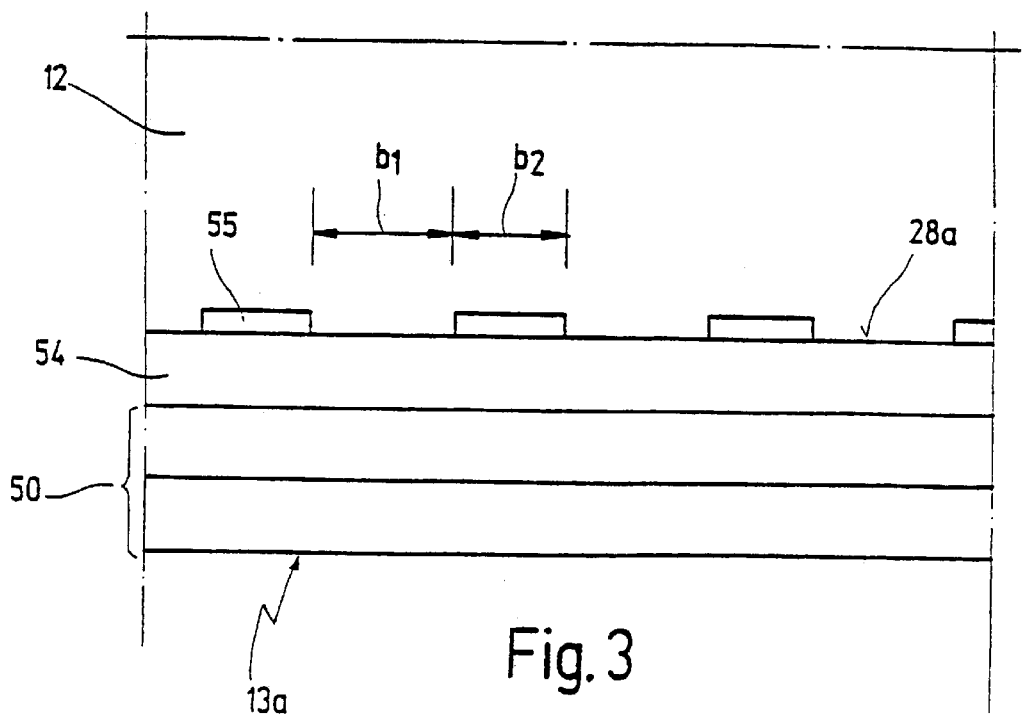
FIG. 3 is a depiction similar to that of FIG. 2, however, for a modified embodiment of the invention.

In the modified embodiment shown in FIG. 3 implant 13a also consists of a plural layer configuration. The lowermost layer is an infrared diode 50. Above that there is a I-layer 54 having a surface 28a. Electrodes 55 are discretely dispersed on surface 28a. Infrared diode 50 in its configuration essentially corresponds to infrared diode 30 in the embodiment of FIG. 2 described above.

Electrodes 55 cover preferably in the order of between 10% and 20% of the implant surface. However, surface ratios of even 50% or more may be used in certain applications.

Electrodes 55 are preferably manufactured by vapor deposition of gold because such gold electrodes are spectrally selectively permeable for visible light. In contrast, electrodes 55 under such circumstance are impermeable to infrared light.

In the embodiment of FIG. 3 the energy supply is, hence, effected by that area fraction of surface 28a being indicated by $b_1$ in FIG. 3. Hence, the resolution of the image is determined by the surface fraction indicated by $b_2$.

The impinging infrared light generates charge carriers within infrared diode 50 such that sufficient energy is available for generating a stimulus at that point when visible light impinges on one or more of electrodes 55. For that purpose layer 54 acts as an electronic switch which may be actuated optically when visible light impinges thereon and through contacts 55. Further details may be taken from co-pending German patent application 195 29 371 of Aug. 10, 1995, the disclosure of which being incorporated herein by way of reference.

For the purposes of energy supply one may, for example, use an infrared diode which is carried by the patient on a spectacle-like device or the like, i.e. a device which is carried close to the eye lens. The infrared diode is directed onto implant 13 or 13a, respectively. When the implant has a diameter of for example 3.0 mm, and output power of the infrared diode in the order of 0.35 mW is considered to be sufficient.

In subretinal implants it may be that under certain circumstances a problem may arise with respect to the biological supply of the retina. This is because in subretinal implants a certain retinal surface is sealed off from below by the implant substrate.

In order to solve these problems, the present invention envisages certain solutions which, however, may also be used independently from the present invention.

According to a first embodiment a retina implant network structure is used. The implant substrate in that case consists of a net-like arrangement. At the positions of the knots within the net photodiodes are located. The knot itself consists of a more or less flexible carrier material. Due to the flexibility the substrate may be better adapted to the shape of the eye background, as compared to rigid implants.

For manufacturing such net-like and/or flexible implants, photodiodes are manufactured on a SOI-layer (silicon-on-insulator), i.e. on a flexible organic foil. Subsequently, they are separated by etching processes and are covered with a lacquer or polyimide layer which, subsequently, is structured. This structured layer may also be used as a mask for etching processes.

In other embodiments utilizing rigid implants the substrate is configured as a solid silicon layer. This substrate may then also be provided with through-holes through which the retina may be supplied with nutrients.

For manufacturing such implant a two-stepped etching process is conducted during the manufacture of the photodiodes. When doing so holes are applied to the silicon surface with a depth of for example 20 μm. When the chips are polished from their backside at a later stage for manufacturing implants, these holes are opened from the backside and may then be used as supplied channels for the retina.

The retina implant may be used within a system for improving vision. The system comprises both the retina implant according to one of the embodiment described before as well as the non-visible light source (in particular the infrared light source).

What is claimed is:

1. A retina implant having a substrate with a first surface for applying same to a retina, said substrate comprising:
   electrode means for stimulating cells within said retina, said electrode means being provided on said first surface and being exposed to visible light impinging on said retina;
   a photovoltaic layer responsive to non-visible light, said photovoltaic layer generating a voltage when said non-visible light impinges thereon, and
   switch means for locally interconnecting said photovoltaic layer with said electrode means, said switch means being controlled by said visible light.

2. The implant of claim 1, wherein said substrate has a second surface and said photovoltaic layer occupies a substantial portion of said second surface.

3. The implant of claim 2, wherein said photovoltaic layer is configured as an infrared diode.

4. The implant of claim 2, wherein said photovoltaic layer is highly dope and has a high lateral conductivity.

5. The implant of claim 1, wherein said switch means is configured as an area in a switch layer of said substrate, said switch layer being electrically non-conductive when exposed to said non-visible light and being electrically conductive when exposed to said visible light.

6. The implant of claim 5, wherein said switch layer is comprised of amorphous, hydrogenized silicon (a-Si:H).

7. The implant of claim 5, wherein said switch layer is comprised of amorphous, hydrogenized silicon (a-Si:H) alloys.

8. The implant of claim 5, wherein said electrode means are configured as surfaces of said areas of said switch layer.

9. The implant of claim 1, wherein said non-visible light is infrared light.

10. The implant of claim 1, wherein said implant is configured as a subretinal implant.

11. The implant of claim 1, wherein said implant is configured as an epiretinal implant and is substantially permeable for said visible light.

12. The implant of claim 1, wherein said substrate is provided with through-openings.

13. The implant of claim 12, wherein said substrate is rigid.

14. The implant of claim 12, wherein said substrate is flexible.

15. The implant of claim 12, wherein said substrate is configured as a net made from a flexible carrier material.

16. The implant of claim 1, wherein said electrode means are configured as an electrode layer.

17. The implant of claim 16, wherein in a top plan view said electrode means are surrounded by said photovoltaic layer.

18. The implant of claim 17, wherein said electrode means occupy between 10% and 50% of said first surface.

19. The implant of claim 16, wherein said electrode layer consists of a metal and is configured to be permeable for said visible light and impermeable for said infrared light.

20. A system for improving vision comprising:
   a retina implant having a substrate with a first surface for applying same to a retina, said substrate including
      electrode means for stimulating cells within said retina, said electrode means being provided on said first surface and being exposed to visible light impinging on said retina;
      a photovoltaic layer responsive to non-visible light, said photovoltaic layer generating a supply voltage; and
      switch means for selectively interconnecting said photovoltaic layer with said electrode means, said switch means being controlled by said visible light; and
   means for applying said non-visible light on said implant.

21. A retina implant having a substrate with a first surface for applying same to a retina, said substrate comprising:
   a first layer being a photovoltaic layer responsive to non-visible light,
   a second layer being electrically non-conductive when exposed to said non-visible light and being electrically conductive when exposed to visible light, said second layer being comprised of amorphous, hydrogenized silicon (a-Si:H), and
   electrodes for stimulating cells within said retina, said electrodes being provided on said first surface and being exposed to said visible light impinging on said retina such that stimuli are exerted on said cells by said electrodes; wherein said stimuli are locally switched utilizing a voltage generated by said first layer, said electrodes comprising a switch, said switch being adapted to be actuated optically and feeding through said voltage as said stimulus when being in a closed state, wherein said switch is configured as an area in said second layer.

22. A retina implant having a substrate with a first surface for applying same to a retina, said substrate comprising:
   a first layer being a photovoltaic layer responsive to non-visible light,
   a second layer being electrically non-conductive when exposed to said non-visible light and being electrically conductive when exposed to visible light, said second layer being comprised of, amorphous, hydrogenised silicon (a-Si:H) alloys, and
   electrodes for stimulating cells within said retina, said electrodes being provided on said first surface and being exposed to said visible light impinging on said retina such that stimuli are exerted on said cells by said electrodes; wherein said stimuli are locally switched utilizing a voltage generated by said first layer, said electrodes comprising a switch, said switch being adapted to be actuated optically and feeding through said voltage as said stimulus when being in a closed state, wherein said switch is configured as an area in said second layer.

* * * * *